United States Patent [19]

Fronk et al.

[11] Patent Number: 5,004,474
[45] Date of Patent: Apr. 2, 1991

[54] PROSTHETIC ANTERIOR CRUCIATE LIGAMENT DESIGN

[75] Inventors: David M. Fronk, Lake Forest, Calif.; David S. Brookstein, Wellesley; John Skelton, Sharon, both of Mass.

[73] Assignee: Baxter International Inc., Deerfield, Ill.

[21] Appl. No.: 442,093

[22] Filed: Nov. 28, 1989

[51] Int. Cl.$^5$ .............................................. A61F 2/08
[52] U.S. Cl. ...................................................... 623/13
[58] Field of Search ............................. 623/13, 11, 20

[56] References Cited

U.S. PATENT DOCUMENTS

| | | |
|---|---|---|
| 3,953,896 | 5/1976 | Treace . |
| 4,149,277 | 4/1979 | Bokros . |
| 4,483,023 | 11/1984 | Hoffman, Jr. et al. ............... 623/13 |
| 4,584,722 | 4/1986 | Levy et al. ............................. 623/13 |
| 4,585,458 | 4/1986 | Kurland . |
| 4,597,766 | 7/1986 | Hilal et al. . |
| 4,605,414 | 8/1986 | Czajka . |
| 4,713,075 | 12/1987 | Kurland . |
| 4,728,329 | 3/1988 | Mansat . |
| 4,744,793 | 5/1988 | Parr et al. . |
| 4,755,183 | 7/1988 | Kenna . |
| 4,759,765 | 7/1988 | Van Kampen ........................ 623/13 |
| 4,772,286 | 9/1988 | Goble et al. . |
| 4,775,380 | 10/1988 | Seedhom et al. . |
| 4,776,851 | 10/1988 | Bruchman et al. . |
| 4,790,850 | 12/1988 | Dunn et al. . |
| 4,828,562 | 5/1989 | Kenna . |
| 4,834,752 | 5/1989 | Van Kampen ........................ 623/13 |
| 4,851,005 | 7/1989 | Hunt et al. . |
| 4,863,471 | 9/1989 | Mansat .................................. 623/13 |
| 4,870,957 | 10/1989 | Goble et al. . |
| 4,894,063 | 1/1990 | Nashef ................................... 623/13 |
| 4,950,293 | 8/1990 | Beacon et al. ........................ 623/13 |

FOREIGN PATENT DOCUMENTS 8709776 7/1987 France .

*Primary Examiner*—Alan W. Cannon
*Attorney, Agent, or Firm*—June M. Bostich

[57] ABSTRACT

An artificial ligament device is provided for joining the ends of two bones wherein at least one of the bones has a tunnel extending therethrough. The device comprises a multilayered or tubular woven ligament having an intra-articular region, at least one bend region, and at least one end region, each region being woven so as to possess qualities of flexibility and strength suitable to the particular types of stresses it receives during use. The end region and a portion of the bend region are encased within a polymer bone block, usually by thermomolding, and the bone block is inserted into the bone tunnel to attach the ligament. The bone block is molded to provide a fixed bend radius for the ligament at the point of exit therefrom so as to control the amount of bending stress on the ligament during flexure and extension of the joint.

83 Claims, 6 Drawing Sheets

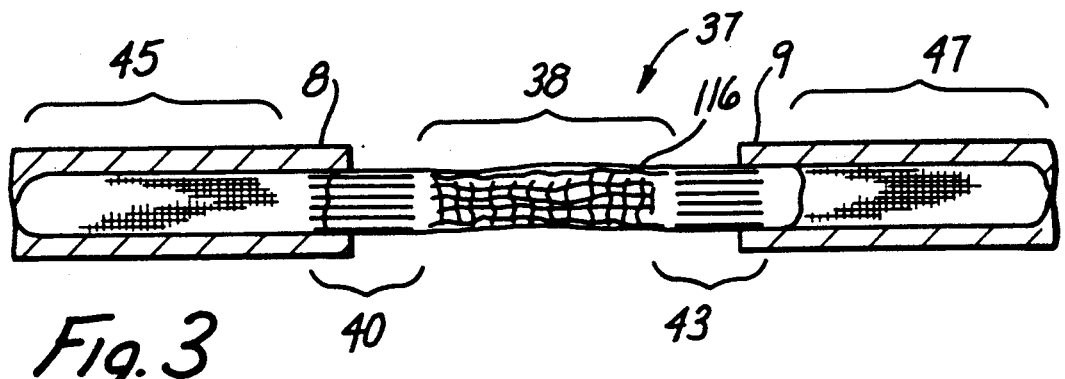
Fig. 3
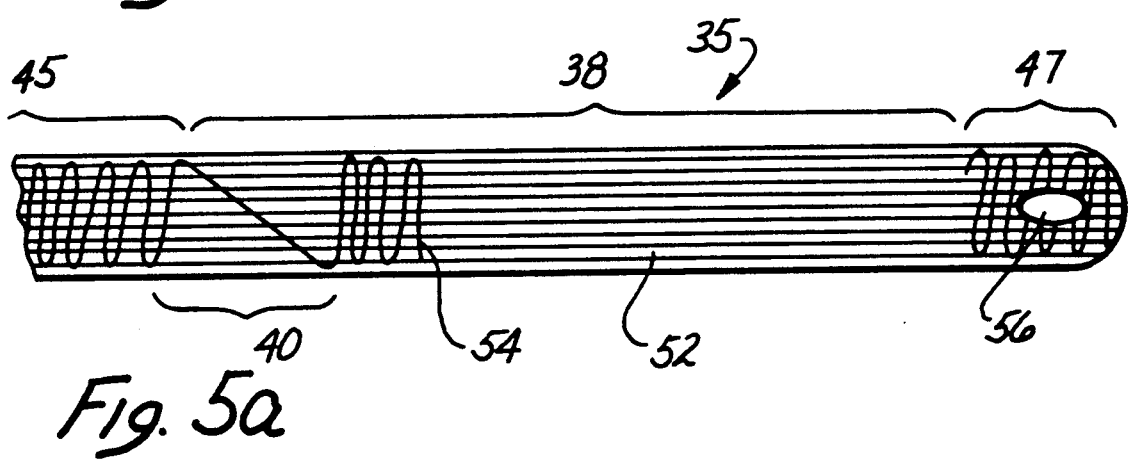
Fig. 5a
Fig. 5b
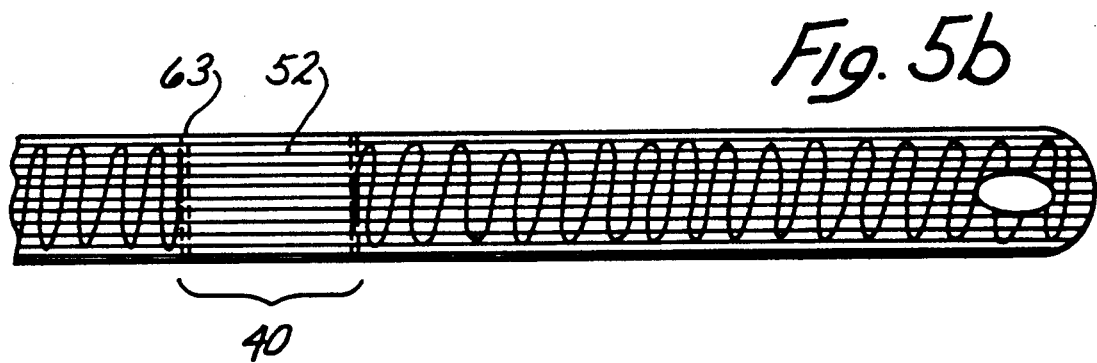
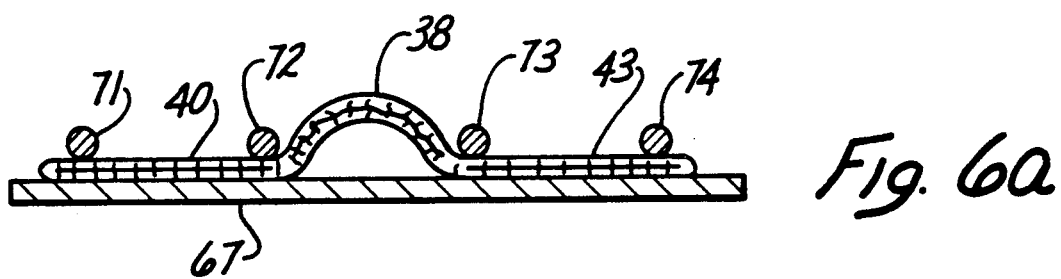
Fig. 6a
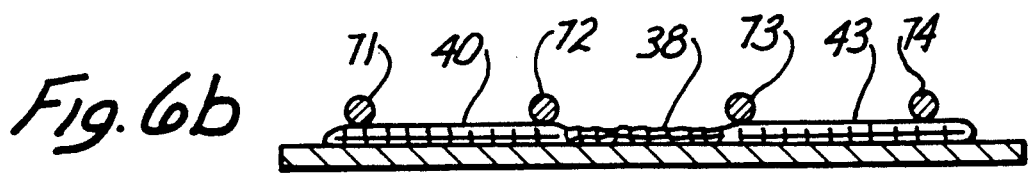
Fig. 6b

PROSTHETIC ANTERIOR CRUCIATE LIGAMENT DESIGN

BACKGROUND OF THE INVENTION

1. Field of the Invention

This invention relates generally to the field of medical prosthetics, and more particularly to a new and improved replacement ligament.

2. Background Information

Replacement ligaments can restore mobility when native ligaments have ruptured beyond repair. However, success of the replacement depends upon proper attachment of the replacement ligament to the host bone and the degree to which the replacement ligament can withstand abrasion during use.

Current designs for emplacement of synthetic ligaments require routing of the ligament through one or two tunnels drilled through bone depending upon whether the over-the-top, modified over-the-top or double tunnel design is employed. In the case of an injured knee joint, the anterior cruciate ligament is replaced by attaching a replacement ligament through tunnels drilled through the femur and tibia from the natural ligament attachment site to an outer surface of the host bone. After passage through the tunnels, the ends of the artificial ligament are usually anchored to the outside of the bones using staples, screws or the like.

The major drawback of such designs is that the ligament moves inside the drilled tunnels during flexion and extension of the knee. If the ligament becomes worn by contact with bone spicules that may form at the entrance to the tunnels, it loses strength and produces particles of ligament debris that cause irritation.

In addition to these drawbacks, the tunnels provide access to the interior of the host bones. As a result, synovial fluid can migrate from the intra-articular region between the host bones into the bone tunnels. Thus, any infection in the intra-articular region can be easily communicated into the interior of the host bones and thereby result in serious intra-osseous complications. Similarly any unhealthy condition within the bones can be communicated to the intra-articular region.

The synthetic ligaments employed in known designs for replacing damaged natural ligaments must meet a wide range of performance requirements, including biocompatibility, high fatigue life, and mechanical properties appropriate to stabilize the involved joint. They are usually constructed of synthetic fibers woven into a cylindrical tube or cord designed to mimic the flexibility and strength characteristics of the natural ligament and to provide sufficient porosity to promote ingrowth of tissue and bone.

Moreover, synthetic ligaments so attached are usually provided with three distinct regions of varying weave structure and porosity designed to meet the requirements of their functions in the three biological regions with which they are in contact. For example, the portion of the ligament which lies between the articular ends of the bones must have high tensile strength and a high degree of abrasion resistance since the intra-articular region includes the portions of the ligament which contact the entrances to the bone tunnels. The portion of the ligament that lies within the tunnels in the bone requires ability to conform to the shape of the tunnel, a minimal elongation under load, and a substantial degree of porosity to enhance ingrowth of bone for permanent fixation of the device to the bone. And the end regions of the synthetic ligament must provide a site having stiffness (minimal elongation under stress) for attachment of the ligament to the bones or for anchorage by tissue and bone ingrowth.

Consequently, it is desirable to have a new and improved replacement ligament and a method for attaching replacement ligaments that overcomes these concerns.

Definitions

As used herein, unless otherwise indicated, the following definitions shall apply:

"Elastic" shall mean the capability of an article to return substantially to its original dimensions after removal of an imposed force which caused deformation of the article. The larger the degree of deformation from which an article can recover, the greater is its "elasticity."

"Elongation" or "elongation under load" shall mean the extent to which an article will deform or stretch under a defined imposed force. "High elongation under load" indicates that the article exhibits decreased tensile stiffness, and "low elongation under load" indicates increased tensile stiffness characteristics.

"Elongation at failure" shall mean the extent to which an article will deform or stretch at the point that it fails.

"Strength" or "tensile strength" shall mean the uniaxial force required to cause failure of an article.

"Tenacity" shall mean the strength of an article per unit of cross-sectional area.

Summary of the Invention

This invention solves the problems outlined above with an artificial ligament device of a generally multi-layered or tubular woven structure wherein the warp yarns are composite, having a higher melting polymer core within a substantially continuous covering of a thermoplastic lower melting polymer, said device comprising:

(a) a ligament having (1) an intra-articular region wherein the warp yarns are crimped so as to provide, within the range of normal physiological loads, a load-percent elongation behavior and an elasticity substantially the same as those of a normal natural ligament of the type that the artificial ligament is intended to replace;

(2) bend regions located on either side of the intra-articular region wherein the degree of crimping of the warp yarns is substantially less than that of the intra-articular region; and (3) end regions located on either side of the bend regions at the two ends of the ligament, wherein the end region is woven under a relatively high warp tension and wherein the degree of crimping is substantially less than in the intra-articular region, thus providing a strong, stiff matrix for thermomold attachment of the end region to a bone block, and (b) at least one bone block of a thermoplastic, low melting polymer fixedly thermomolded to an end of the ligament so that a portion of the bend region extends from the bone block while the remaining portion of the bend region and at least a portion of the contiguous end region of the ligament are fixedly encased therein, wherein the bone block has a permanent bend radius at the point of attachment of the ligament thereto.

BRIEF DESCRIPTION OF THE DRAWINGS

FIG. 3 is an illustration of an artificial ligament device with a longitudinal section through the axis of cylindrical bone blocks.

FIGS. 4 and 5 are plan views of the artificial ligament of the present invention showing the various regions and sections of the ligaments.

FIG. 6a is a side view of the ligament bound in a heat-setting device prior to the heatsetting step in a method of the present invention.

FIG. 6b is a side view similar to FIG. 6a illustrating the ligament after the heatsetting step in a method of the present invention.

DETAILED DESCRIPTION OF THE INVENTION

Figure 1:
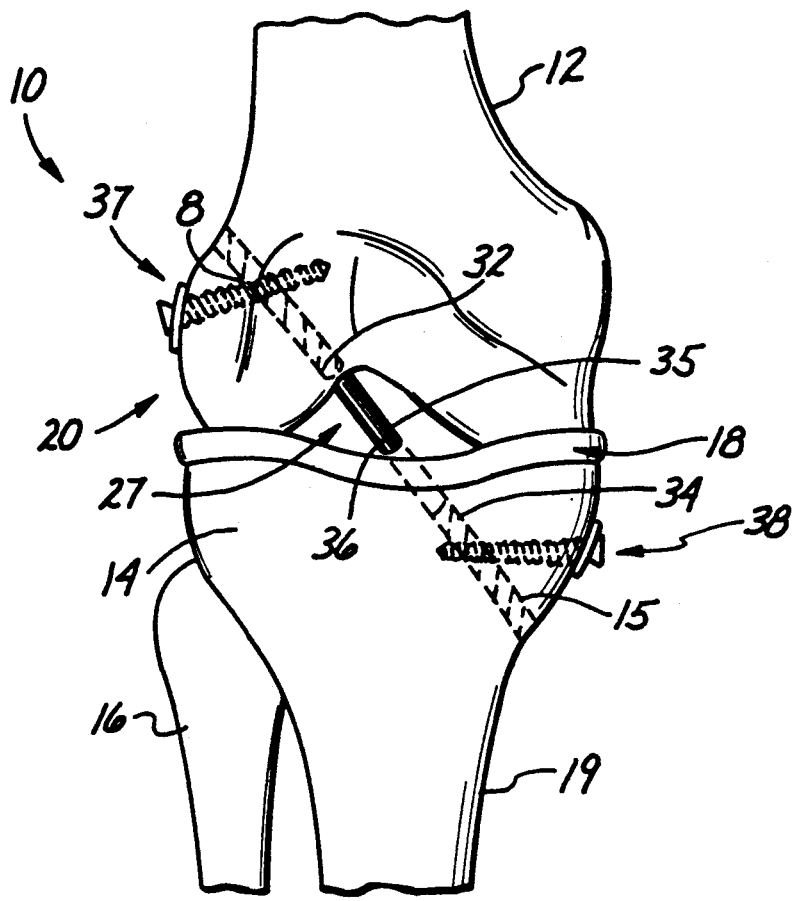
FIG. 1 is a front perspective view of a knee bone structure illustrating the general placement of an artificial ligament device having two bone blocks in a double tunnel configuration.

The artificial ligaments of this invention can be made from any biocompatible material that has mechanical properties which simulate those of the natural anterior cruciate ligament, for example, the artificial ligaments can be woven from a variety of synthetic fibers and can comprise five or more regions having elasticity, porosity and strength tailored to the specific functions they are to serve, as is preferred herein.

The artificial ligament is differentiated into five regions. One generally central region is located so as to pass through the space between the two bones to be connected thereby, for instance, the intra-articular region of the knee joint. This region is referred to herein as the intra-articular region of the artificial ligament. On either side of the intra-articular region are two regions referred to as the bend regions because in use they are located at the point where the ligament and attached bone blocks exit the tunnels in the bones of the host. At these points the ligament undergoes great bending stresses. And on either side of the bend regions lie two terminal regions called herein the end regions of the ligament. In use, the end regions lie completely within the bone blocks, which in turn are placed into tunnels in the two bones that the artificial ligament serves to attach together.

Each of the three types of regions requires specialized properties designed to enhance the function of the artificial ligament. The intra-articular region requires a relatively high degree of elongation under load to achieve natural joint movement and to relieve stresses on the artificial ligament and associated natural ligaments. The bend regions of the ligament require inelasticity to assure secure attachment of the ligament to the bone blocks and durability to bend loading to assure a long operational life for the ligament. And the end regions require inelasticity to assure secure attachment of the ligament to the bone block.

The multi-regioned ligaments of this invention are similar to those disclosed in co-pending U.S. patent application Ser. No. 412,756, filed Sep. 26, 1989, which is incorporated herein by reference in its entirety, wherein yarns spun from high-tenacity, inelastic fibers can be used for construction of both the elastic and inelastic regions of the artificial ligament. However, in this invention it is preferred that the ligament be woven from a combination of at least two different biocompatible fibers having melting points sufficiently separated that the fibers in the ligament having the lower melting point can be melted without melting or weakening the higher melting point fibers. The function of the lower melting point fiber included in the weave making up the ligament is twofold. First, the lower melting fiber provides a means for securely attaching the ligament to a low melting-point bone block by a process of thermomolding. During thermomolding the lower melting fibers in the ligament and the low melting thermoplastic substance of the bone block sufficiently melt together to provide secure and lasting attachment of the bone block to the ligament. Secondly, the lower melting fibers in the ligament can be sufficiently melted during the thermomolding step to form a substantially continuous covering for the stronger, load-bearing higher melting fibers.

The lower melting point fibers are biocompatible thermoplastic polymers having a melting point temperature of from 10 to 100 Centigrade degrees lower than the temperature of the particular higher melting fiber selected. As used herein thermoplastic polymers are those which can be repeatedly heated to the melting temperature without losing their capacity to be remolded to new shapes. A preferred lower melting fiber is styrene-ethylene/butylene, styrene block copolymer with polydimethylsiloxane and other modifiers available from Concept Polymer Technologies, Inc. (Clearwater, FL) under the trademark C-Flex ®, which has a melting point of from 160 to 200 degrees Centigrade.

Preferred higher melting point fibers for the preparation of these artificial ligaments are biocompatible, heat-settable polyethylene terephthalate fibers. Heat-settable fibers are those having a marked glass transition temperature below the melting point temperature. These fibers are well-known in the textile arts and are commercially available. Because of the high loads placed on artificial ligaments, particularly those of the knee, the higher melting fibers should have high tensile strengths (tenacities). The preferred higher melting point fiber is available from E.I. du Pont de Nemours and Co., under the trademark Dacron ® type 52B, which has a melting point of between about 199 and 230 degrees Centigrade.

Commercially available Dacron ® type 52B yarns are 55/27, 110/34, 140/68, 350/100 and 1060/192 (expressed as yarn denier/number of filaments). A particularly preferred higher melting yarn is Dacron ® type 52B 350/100.

Continuous filament yarns, prepared from fibers ranging in diameter from about 50 to about 1100 denier, are advantageously employed for both the warp and filler strands, and a single strand may contain from about 20 to about 200 individual filaments ranging in diameter from about 1.5 to about 40 denier. However, in this invention the fibers to be used as the warp, or primary load-bearing fibers, during the weaving step contain commingled therein both the lower melting and higher melting fibers described above. The commingled fibers are formed by a process in which the lower and higher melting fibers are so combined that during the thermoplastic molding step the lower melting fibers will melt and intimately encompass the higher melting fibers, preferably with the result that each higher melting fiber becomes encased within a coating of the lower melting substance. Thus, the commingled fibers become composite fibers (i.e., an inner core of higher melting polymer surrounded by a substantially continuous coating of lower melting polymer) during the thermomolding step as described hereinafter.

Various methods can be used to prepare the commingled fibers. In one method, the lower melting fibers can be twisted about an untwisted core of higher melting fibers. For example, the C-Flex ® fibers can be twisted about an untwisted core of Dacron ® 52B. This procedure prevents twist-induced torsional stresses that might make the artificial ligament torsionally unstable. Alternatively, if the twisting operation does not result in an intimate enough combination of the two fibers in the thermoplastic molding step, a commercially available "commingler" machine for commingling the fibers, such as that available from Concordia Yarns (Coventry, RI), can be employed.

During the weaving step, the filling fibers can be either the above-described commingled fibers or not, but generally the complexity of the weaving operation is advantageously reduced if only the lower melting fibers are used as the filling fibers. The commingled warp yarns and lower melting or commingled filler yarns are woven into tubular or multilayered forms using conventional procedures and equipment to achieve the distinct features of the different regions of the multi-regioned artificial ligament (i.e., by varying the physical configuration of the yarns and the weaving conditions). The features to be controlled include the size, tensile strength, abrasion resistance, porosity, and stress-strain characteristics. In general, these features are controlled by manipulating the yarn tension, yarn crimp, number of picks per inch, yarn size, filling yarns, and number of yarns. In general, these features are controlled by manipulating the number and size of warp yarns, the warp and filing tensions and the number of picks per inch, which in turn control the crimp balance in the structure. In addition, the extent of stretch or shrinkage which is allowed during a post-weaving heat-setting step influences the physical properties of the prosthetic ligament.

Referring to FIG. 1, a knee joint is illustrated and designated by the reference numeral 10. The knee joint 10 is defined generally by the junction of a femur 12 in the upper leg of a person, and a tibia 14 together with a fibula 16 in the lower leg of the person. The contacting surfaces of the femur 12 and the tibia 14 are cushioned and lubricated by cartilage shown generally at 18.

The femur 12 is the largest bone in the human body and terminates in the region of the knee joint 10 in a pair of large knobs or condyles 20. A smooth articulating surface extends beneath the condyles and defines a condyle trench 25 between the condyles 20. An intra-articular cavity 27 exists between the femur 12 and the cartilage 18. This cavity 27 is defined primarily by the space which exists between the cartilage 18 and the elevated condyle trench 25.

In a typical replacement of the anterior cruciate ligament, a tunnel 32 is drilled through the femur 12 and a tunnel 34 is drilled through the tibia 14. The tunnel 32 is drilled from the outer surface of the femur 12 through the condyle 20 and exits into the intra-articular cavity 27. Similarly, the tunnel 34 is drilled through the outer surface of the tibia 14 through the cartilage 18 and exits into the intra-articular cavity 27.

Figure 2:
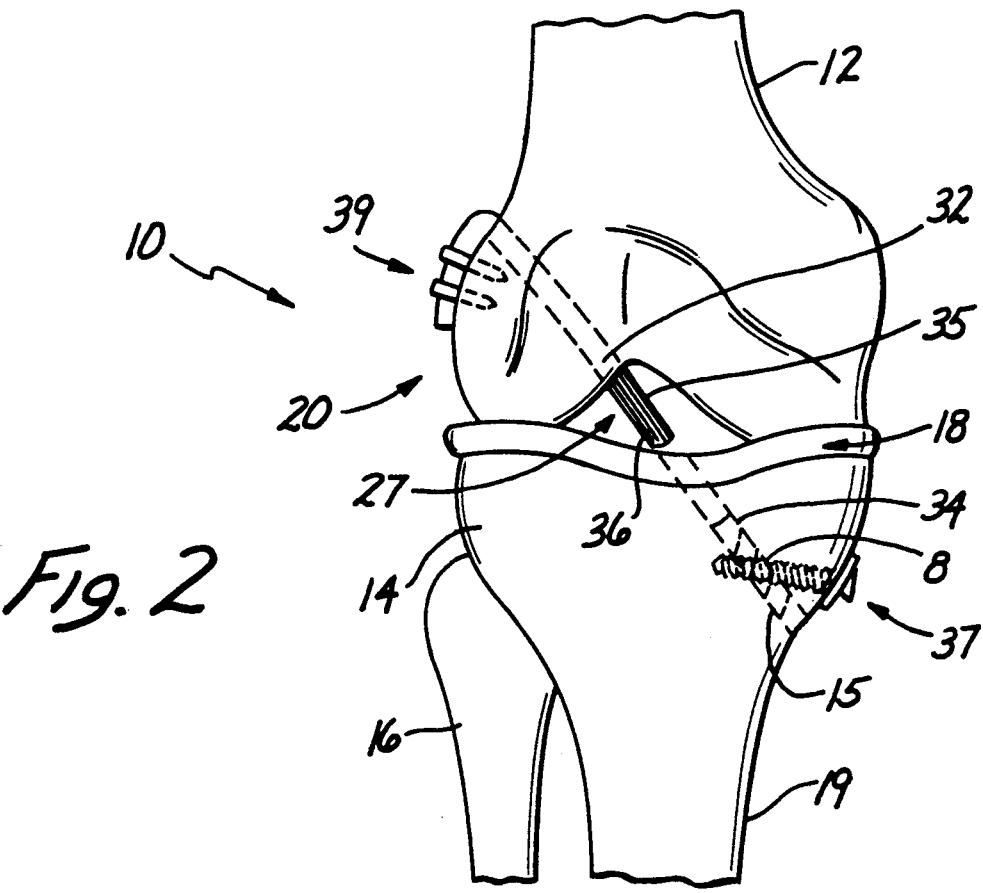
FIG. 2 is a front perspective view of a knee bone structure illustrating the general placement of an artificial ligament device having a single bone block in a double tunnel configuration.

An artificial ligament device 36 of the present invention is installed with bone blocks 8 and 9 inserted into tunnels 32 and 34 with ligament 35 extending therebetween. Means for securing bone blocks 8 and 9, shown generally at 37 and 38, may include a screw and washer combination. Alternatively, as shown in FIG. 2, device 32 utilizes a single bone block 8 installed in tunnel 32 and secured by means 37 and ligament 35 extends therefrom through tunnel 34 and is secured on the outer surface of tibia 14 by means, such as a pair of staples, shown generally at 39.

A preferred embodiment of the ligament device 36 is illustrated in FIG. 3 and includes an intra-articular region 38 disposed between two bend regions 40 and 43. The ends of the ligament 35 terminate at respective end regions 45 and 47. The bend regions 40 and 43 are provided with special characteristics in accordance with the present invention. The bone blocks 8 and 9 are shown in cut-away to illustrate that the ends of the ligament 35 are encased within the bone block 8 and 9 respectively and exit therefrom about mid-point in the bend regions 40 and 43. The bend regions are provided with special characteristics in accordance with the present invention. As shown in FIGS. 3 and 4 the ligament 35 typically includes a multiplicity of warp yarns 52 which extend longitudinally of ligament 35, and at least one fill yarn 54 inter-woven in the warp yarns 52 in a configuration dependent upon the characteristics desired for the various regions of the ligament 35.

In operation, the intra-articular region 38 of the ligament 35 is disposed within the intra-articular cavity 27 between the ends of the femur 12 and tibia 14. The bend regions 40 and 43 are disposed to extend from the intra-articular cavity 27 into the respective bone blocks 32 and 34. This leaves end regions 45 and 47 to extend within the respective bone blocks 8 and 9 which are installed into bone tunnels as illustrated in FIG. 1.

The bend regions 40 and 43 are advantageously provided in those locations where significant bending occurs, that is, where the ligament exits from the bone blocks 8 and 9.

The intra-articular region has a higher degree of elasticity than the end sections of the artificial ligament. The elasticity of the intra-articular section preferably closely simulates that of the natural ligament being replaced. In general, the elasticity is represented by an elongation factor of from about 20% to about 50% at failure. Within the range of normal physiological loads (i.e.. those encountered in vivo by a normal ligament of the type being replaced); the elongation-load behavior of the intra-articular region is substantially similar to that of the natural ligament being replaced. This region has the highest elongation under load of the various regions of the artificial ligament.

The intra-articular region has a relatively small cross-sectional area and has a high aspect ratio, approximating that of the natural ligament being replaced. For a prosthetic cruciate ligament of the knee, the diameter usually ranges from about 4 mm to about 8 mm, preferably from about 4 mm to about 5 mm. The length of this region will vary, depending upon the physiological dimensions. For a prosthetic anterior cruciate ligament, typical lengths range from about 30 to about 36 mm. The tensile strength of this section is preferably higher than that of the natural ligament. Tensile strengths of at least about 2000 Newtons, preferably at least about 3500 Newtons are generally obtained. The intra-articular region also is characterized by a high degree of elasticity. Advantageously, this region can recover to substantially its original dimensions after being subjected to repeated cycles of 25% of the tensile failure load.

The low porosity and resistance to abrasion and fraying of the intra-articular region are promoted by employing a tightly woven structure. A warp density ranging from about 800 to about 1200, preferably about 1000 yarns per inch, and a pick density ranging from about 40 to about 70 picks per inch, preferably from about 50 to 60 picks per inch, are used to achieve the tightly woven structure.

Figure 13:
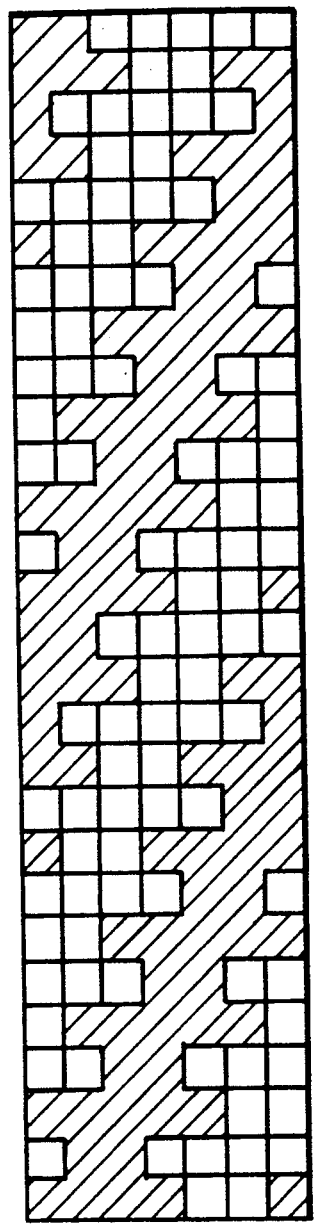
FIG. 13 is a schematic depiction of a 5-1-1-5 broken twill weave pattern that can be employed in weaving the ligament of the present invention.

The high elongation under load of the intra-articular region is achieved by arranging the warp yarns in a highly crimped configuration, which is achieved by the weave pattern employed and by the use of a relatively low warp tension and a relatively high filling yarn tension. A preferred weave pattern is illustrated in FIG. 13 of the drawing. This weave pattern is sometimes referred to as a 5-1-1-5 broken twill and achieves a high degree of elongation under load in the longitudinal direction, while maintaining a relatively undeformable structure in the radial direction.

Those skilled in the art will appreciate that other weave patterns employing low warp tensions and high filling yarn tensions may also be employed to achieve the desired elongation under load characteristics. As depicted in FIG. 6a (in slightly exaggerated form), the warp yarns are highly crimped, and weft yarns are relatively uncrimped. However, it should be noted that the high elongation under load and the highly crimped configuration will be affected if the intra-articular region is subjected to a subsequent heat-setting step.

The actual warp and filling yarn tensions employed will depend upon the weave pattern, the particular type and size of yarn used and the degree of crimp desired. In general, for the preferred warp yarns in the preferred configurations, such warp tensions will range from about 0.01 to about 0.05 lb. per yarn end, and the filling yarn tension will range from about 0.05 to about 0.5 lb. per yarn end. These tensions may vary considerably, depending on the particular yarns employed, and the weaving conditions and equipment.

Unlike the intra-articular region of the ligament, the bend region of the ligament, which runs within the bone block and extends immediately therefrom, requires durability to bend loading and low elongation under load. In the three views of FIG. 4, the knee joint 10 is shown with the femur 12 and tibia 14 illustrated with various degrees of flexure. More specifically, in FIGS. 4a, 4b and 4c, the flexure angle between the femur 12 and tibia 14 are illustrated at zero degrees, 90°, and full flexure, respectively. The position of the tunnels 32 and 34 with respect to the femur 12 and tibia 14 respectively, is also illustrated. These views are helpful in analyzing the flexure angles a ligament undergoes with respect to the tunnels 32 and 34.

The angle of the ligament 35 as it enters the tunnel 32 is referred to as the femoral angle $a_F$. Similarly, the angle between the ligament 36 and the is referred to as the tibial angle $a_T$.

Both of these angles, $a_F$ and $a_T$ are measured from a moveable axis which is defined by the position of the intra-articular region within the intra-articular cavity 27. These angles are best illustrated in FIG. 4c.

Figure 4A:
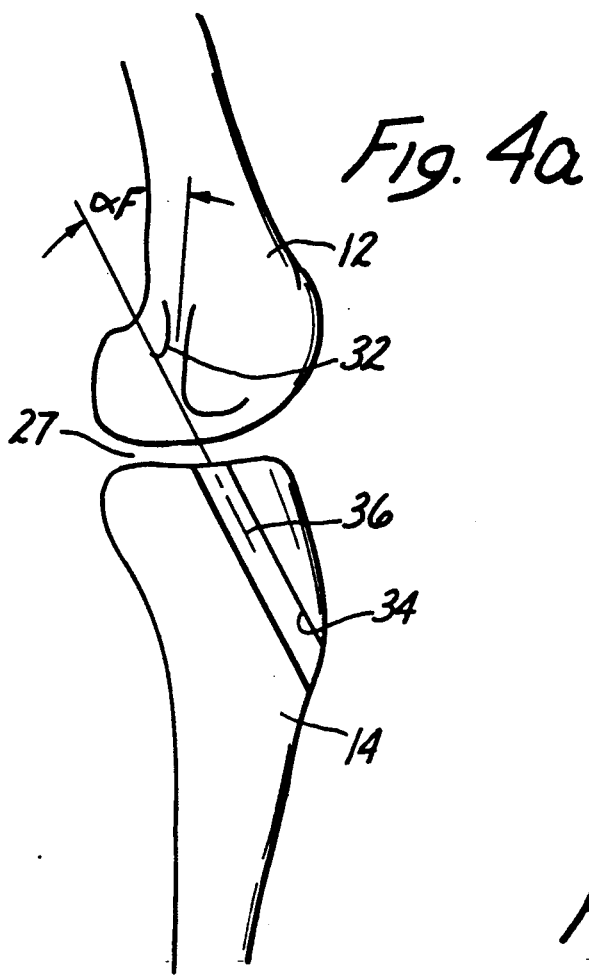

At the point of zero flexure, as illustrated in FIG. 4a, the tibial angle $a_T$ is substantially zero. However, the femoral angle $a_F$ is approximately minus 30°.

Figure 4B:
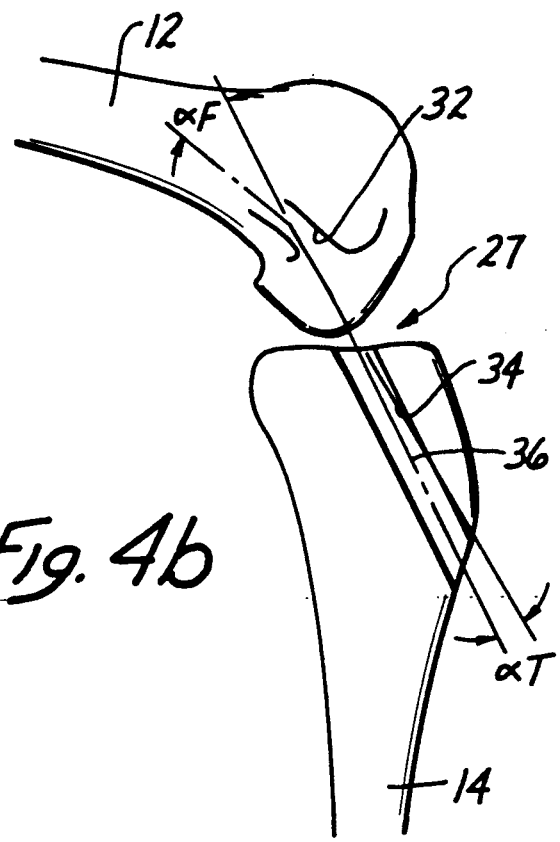

As the femur 12 pivots 90° relative to the tibia 14, as illustrated in FIG. 4b, the tibial angle opens to approximately 20° and the femoral angle passes across the axis to about plus 20°. Thus with 90° flexion, the ligament 35 undergoes a tibial angle change of approximately 20° while the femoral angle undergoes a change of approximately 40°.

Figure 4C:
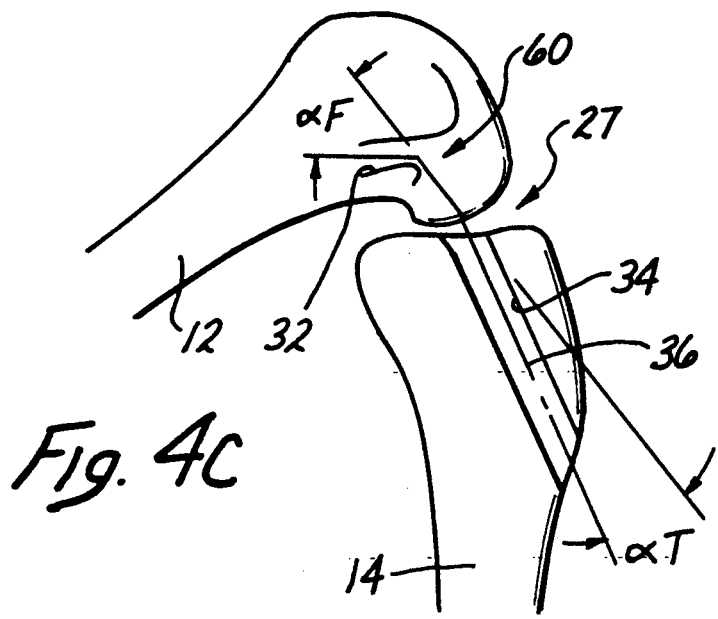

At full flexion, illustrated in FIG. 4c, the tibial angle stays at approximately 20° and the femoral angle expands to approximately 50°. From these views it is now apparent that the ligament 35 must be capable of bending from zero degrees to full flexion through an angle of approximately 20° with respect to the tibia 14 and approximately 80° with respect to the femur 12. These bending or flexure angles are particularly severe when the ligament 35 must bend around a narrow radius such as that shown generally by the reference numeral 60 in FIG. 4c where the tunnel 32 joins the outer surface of the femur 12. In accordance with the present invention, bend regions 40 and 43 are specifically configured to accommodate this flexure.

The bend regions 40 and 43 are best illustrated in FIG. 5a wherein the warp yarns 52 are shown to extend longitudinally through the entire ligament 35. It is the fill yarn 54 which undergoes the primary change in the bend regions 40 and 43. Whereas this fill yarn 54 is woven with approximately 40 to 70 picks per inch throughout the ligament 35, in the bend regions 40 and 43, the fill yarn 54 is woven with a pick density of only about 0 to 8 picks per inch, and preferably about 0 to 3 picks per inch. In FIG. 5a, bend region 40 is illustrated to have only one pick over its preferred length of 20±10 mm.

The advantage of this loose weave in the bend region is to significantly reduce the binding affect of the fill yarn 54 so that the warp yarns 52 in this region can spread out and thereby more easily accommodate a flexure angle.

FIG. 5b illustrates a further embodiment of the invention wherein the fill yarn 54 is actually cut at either end of bend regions 40 and 43. In this particular embodiment, there is a total absence of weaving within the bend regions and the warp yarns 52 are not laterally bound by any fill yarn.

As is discussed more fully hereinafter, in one embodiment of the invention a bone block is attached to only one end of the ligament. In this embodiment of the invention, it is within the scope of this invention to omit the bend region from the end of the ligament having no bone block attached. In this case, the length of the intra-articular and/or the end region can be increased to accommodate for absence of the second bend region.

The low elongation under load of the bend region is achieved by arranging the warp yarns in a configuration in which the crimp is low. Since these yarns are spun from substantially inelastic fibers, the uncrimped yarns are inelastic and exhibit a low elongation under load. The elongation factor for this region of the artificial ligament preferably is less than about 15%, more preferably less than about 10% at failure.

The physical dimensions of the bend regions are controlled by those of the bone blocks into which they are placed and, consequently by those of the bone tunnels into which the bone blocks will be placed during surgery. These dimensions may vary, depending upon the particular application and the preferences of the surgeon. In general, however, the diameter of the bend region ranges from about 6 to about 12 mm, preferably from about 6 to about 8 mm for a prosthetic anterior cruciate ligament of the knee. The length of this region also may vary substantially, and typical lengths for prosthetic anterior cruciate ligaments range from about 30 mm to about 70 mm.

The two end regions of the artificial ligament are designed for stiffness, strength and for attachment during the thermoplastic molding step to at least one, and preferably two, synthetic bone blocks so that the interface between the bone block and the ligament provides the rigidity found in the Sharpey's fibers that form the natural interface between bone and ligament. Accordingly, the end regions are tightly woven from substantially uncrimped yarns using relatively high warp tensions, and therefore, they have very low elongation values. The high yarn density and low porosity provide strength and allow for secure attachment between the ligament and the synthetic bone blocks. Reinforcing fibers or biocompatible plastic reinforcing members, and the like, may be woven into these end regions to enhance their strength.

Each of the regions of the artificial ligament is optionally separated from adjacent regions by short transitional regions (not shown). In these transitional regions, the yarn types, the pick density and the warp tension may gradually change from values for one region to the values for the adjacent region. These transitional regions generally do not exceed about 5 mm in length. As illustrated in FIGS. 5a and 5b, the warp yarns, which are the primary load-bearing yarns, are continuous throughout the length of the artificial ligament. This configuration provides maximum strength and avoids weak regions in the transitional regions. Inasmuch as the warp yarns are uncrimped in the end regions and are crimped in the intra-articular region, each length of yarn is treated to have both crimped and uncrimped portions of appropriate lengths.

The method of making the multi-regioned woven ligament up to the point of the thermomolding step, which converts the commingled fibers into composite fibers and molds the ligament within the bond block, is disclosed in copending U.S. patent application Ser. No. 412,756 filed on Sep. 26, 1989, as mentioned above. However, it should be noted here that the mechanical properties of the artificial ligament are substantially improved by subjecting the woven ligament to a heat-setting treatment. Generally the heat-setting step increases the elongation under load of the intra-articular region and stiffens and maintains or actually decreases the elongation under load of the bend and end regions.

The heat-setting step involves heating the ligament under controlled conditions of restraint for a time and to a temperature sufficient to produce a transition within the molecular structure of the heat-settable fiber to a substantially glassy state.

Not all polymers are heat-settable, but among those which are, the heat-settable temperature, which is below the melting point, is characterized by a marked transition of the molecular arrangement to an amorphous or glassy state and can be determined empirically. The heat-setting step herein is accomplished by constraining the bend and end regions against substantial longitudinal movement, as by applying a tension thereupon, while allowing the intra-articular region to remain unconstrained. One method for performing the heat-setting step involves employing the device illustrated in FIGS. 6a and 6b. The entire woven artificial ligament is placed on a heat-conductive (e.g., metal) plate 67, and bars 71, 72, 73 and 74 are used to securely clamp the ligament in place. The bend and end regions are stretched between bars 61 and 62 between bars 73 and 74, such that these regions of the ligament are is also illustrated in FIG. 6a, prior to the heating, the intra-articular region 38 is formed into a loose loop, such that it is substantially constrained. Then, the entire ligament is subjected to a heat-setting temperature so that the bend and end regions stiffen while the warp yarns in the intra-articular region crimp even more than was accomplished during the weaving procedure. This crimping causes the length of the intra-articular region to shrink. The configuration of the ligament after the heat-treating step is illustrated in FIG. 6b.

One method for accomplishing heat-setting is to place the device illustrated in FIGS. 6a and 6b into a convection oven raised to a heat-setting temperature. The times and temperatures employed in the heat-setting step can readily be determined empirically. Such temperatures may vary, depending upon the physical properties of the particular yarn employed, the size of the artificial ligament and the ultimate properties desired. In general, the heat-setting temperature selected is sufficiently high to cause the yarns in the intra-articular region to crimp, yet not so high as to cause melting or weakening of either the lower melting or higher melting fiber. Typically the heat-setting temperatures will range from about 130 to about 160, and preferably from about 135 to about 155 degrees Centigrade.

The ligament is heated for a time sufficient to accomplish the desired degree of crimping in the intra-articular region. Such time generally ranges from about 1 minute to about 20 minutes, preferably from about 3 to about 8 minutes, depending upon the temperature, yarn types, ligament size, etc. For an anterior cruciate ligament of the knee having Dacron ® 52B as the higher melting fiber, heat setting at 180 degrees Centigrade for about 5 minutes has been found to produce favorable results.

Alternatively, and preferably, heat-setting of the ligament is accomplished during the thermomolding step as is described below.

Prior to use, at least one end of the synthetic ligament is fixedly and rigidly attached to a synthetic bone block made from a biocompatible material having mechanical properties that mimic those of the natural bone into which it is to be inserted. The bone block should have a mechanical stiffness of at least about 1500 Newtons per millimeter. Preferably, a low melting thermoplastic polymer is used to make the bone block. Most preferably the bone block is formed from C-Flex ®, a silicone-modified thermoplastic elastomer described above.

Figure 7:
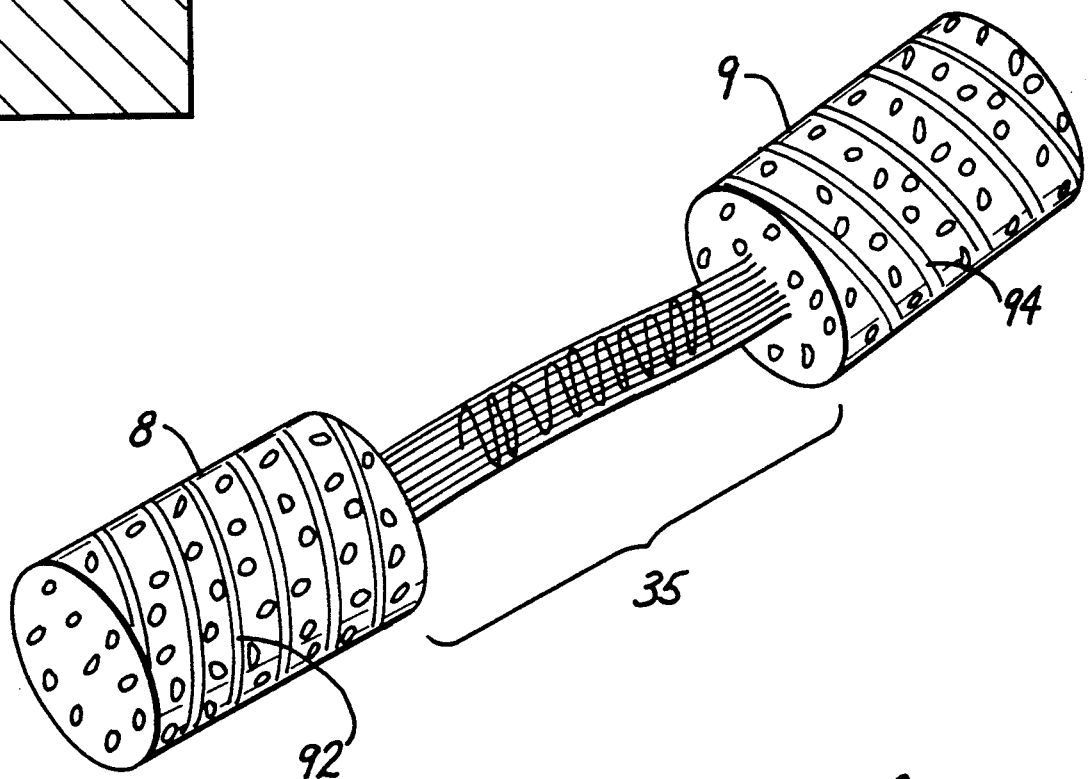
FIG. 7 is a perspective view of an artificial ligament device with two molded bone blocks having a porous surface with threads molded therein.

Generally, the external size and shape of the bone block are selected to conform to those of the borehole to receive it. Usually, however, the bone block is elongate and in the shape of a circle, square, or rectangle in the cross-section. Preferably, as shown in FIG. 7, the bone blocks 8 and 9 have the shape of a solid right cylinder, having a right cross-sectional diameter of between about 6 and 14 mm, preferably between about 8 and 12 mm. The length of the cylinder is generally between about 20 and 50 mm. The bone blocks 8 and 9 can be made long enough so that when it is placed flush with the entrance into one end of the borehole, a portion thereof protrudes at the other entrance. This extension can be removed by the surgeon once the bone block has been fixedly attached to the host bone, for instance, by sawing it off. Alternatively, the molded bone block with ligament attached can be reheated by any conventional means such as a convection oven and modified in shape prior to emplacement, for example, in the operating room, to enhance its secure attachment into the host bone. Reheating of the molded bone block, however, must be to a temperature sufficiently below that at which the bone block and/or lower melting fiber will begin to flow so that the bone block can be reshaped without any weakening of the attachment of the ligament to the bone block(s).

Figure 8C:
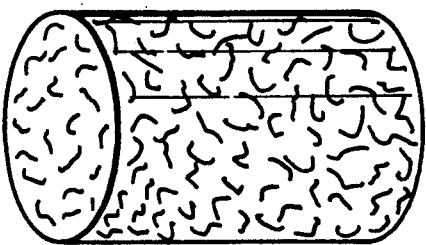
FIGS. 8a, 8b and 8c are perspective views of molded bone blocks having uneven surface features molded therein.
Figure 8B:
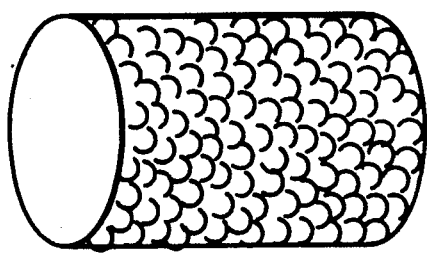
Figure 8A:
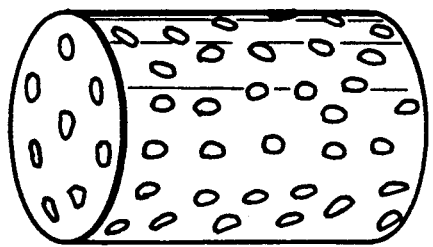

The outside surface of the formed bone block has two important features that are molded into the bone block during the thermomolding step. Optionally, but preferably, the outer surface of the formed block has a generally uneven or porous finish for promoting ingrowth of the host bone into the bone blocks. For example, as shown in FIG. 8, the outside surface of the bone block can be provided with raised beads (FIG. 8a), porelike depressions (FIG. 8b), or fibrous protuberances (FIG. 8c) for enhancing bony ingrowth of the host bone into the synthetic bone block. The pores or depressions for promoting bone ingrowth are generally between about 100 microns to about 400 microns in diameter and in depth or height. These surface features are provided by means (not shown) located in the inner surface of the mold used during thermomolding.

Figure 9:
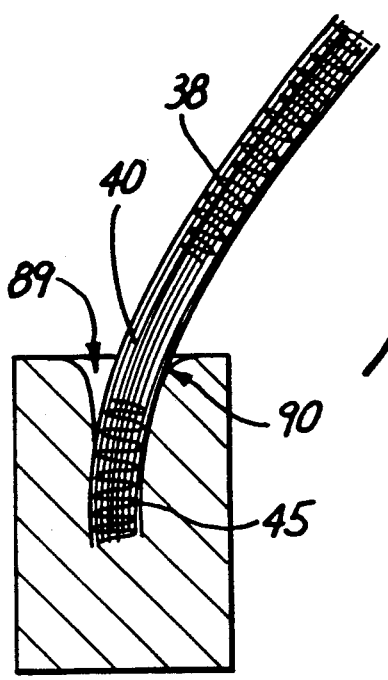
FIG. 9 is a cross sectional view of a ligament and bone block showing the permanent bend radius molded into the bone block and the location of the bend region in the ligament.

The second, critical feature of the bone block is, as shown in FIG. 9, a generally convex curved surface feature 90 located at the point of attachment of the ligament to the bone block for providing a permanent bend radius for the ligament during use. The permanent bend radius eases the bending stress created in the synthetic ligament at the point of attachment and reduces wear in the ligament caused by abrasion against the bone block. The length of the permanent bend radius is selected to enhance the bending fatigue life of the ligament and is usually between about 1.5 and 3 mm. As shown in FIG. 9, the point at which the ligament protrudes from the end of the bone block is optionally and preferentially recessed into a generally conical declivity 89, the interior side of which has a raised portion to provide the convex curved surface feature 90 of permanent bend radius. As is disclosed below in the description of the thermomolding step, the permanent bend radius is usually molded into the bone block during the thermomolding step.

In addition to the above surface features generally formed during thermomolding, the surface of the bone block can be coated, impregnated with or otherwise treated with an osteo-conductive material (not shown), such as hydroxyapatite, calcium phosphate, and the like, to improve the bony ingrowth.

Whether one or two bone blocks are molded onto the ligament will depend upon the surgical procedure in which the prosthetic anterior cruciate ligament is to be used. In the "over the top" procedure, only one bone block is used and the ligament is long enough so that the bone block can be fastened with a screw into a bone tunnel in the tibia while the ligament is passed through the intra-articular space, wrapped around the femoral condyle, and fastened directly to the outside of the femoral condyle by a permanent fastening means, such as a screw or staple. Usually however, a bone block is molded to each end of the ligament using the procedure described below.

Figure 10:
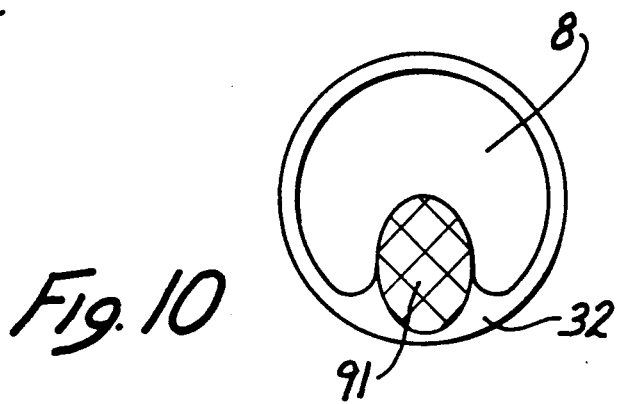
FIG. 10 is an axial cross-sectional view of a cylindrical bone block and bone tunnel showing the bone block modified to accommodate an interference screw.

The molded bone block and ligament device is surgically emplaced using generally the procedures developed for implanting a host-donated ligament with attached native bone plugs. Generally, as described above with reference to FIG. 1, the ligament is threaded through the intra-articular space, and the bone plugs are inserted into tunnels drilled into the tibia and femur of the host where they are permanently fixed into place by means of a permanent fastening device, such as a screw. Alternatively, the shape of the bone block 8 can be modified as shown in cross-sectional view in FIG. 10 to accommodate an interference screw 91 placed alongside the bone block 8 in the bone tunnel 32 as a means of permanently fixing the bone block 8 into the bone tunnel 32.

Several embodiments of the prosthetic anterior cruciate ligament device of this invention are designed to mimic the torsional aspects of the native anterior cruciate ligament. For instance, it is also within the scope of this invention to mold threads into the exterior surface of at least one of the bone blocks so that during emplacement of the ligament one or both bone blocks can be screwed into their respective bone tunnels to adjust the torsion in the ligament and then optionally attached by a screw.

In one embodiment of the invention, shown in FIG. 7, the ligament has cylindrical bone blocks of different diameter molded onto its ends, with the femoral bone block 8 having the smaller diameter and having right hand threads 92 molded into its side and with the tibial bone block 9 having left hand threads 94 molded into its side. This embodiment of the device can be emplaced by threading the smaller femoral bone block with attached ligament sequentially through the tibial bone tunnel and the intra-articular space, and by screwing the femoral bone block into an appropriately sized femoral tunnel with a right handed turning motion. The larger, tibial bone block is then screwed with a left hand motion into a bone tunnel of suitable diameter in the tibia. One or both bone blocks are then optionally attached using a bone screw as above described. These synthetic ligament devices and the above methods of emplacing them allow both tension and torsion to be placed on the ligament so as to mimic that found in a healthy, native anterior cruciate ligament.

Figure 11:
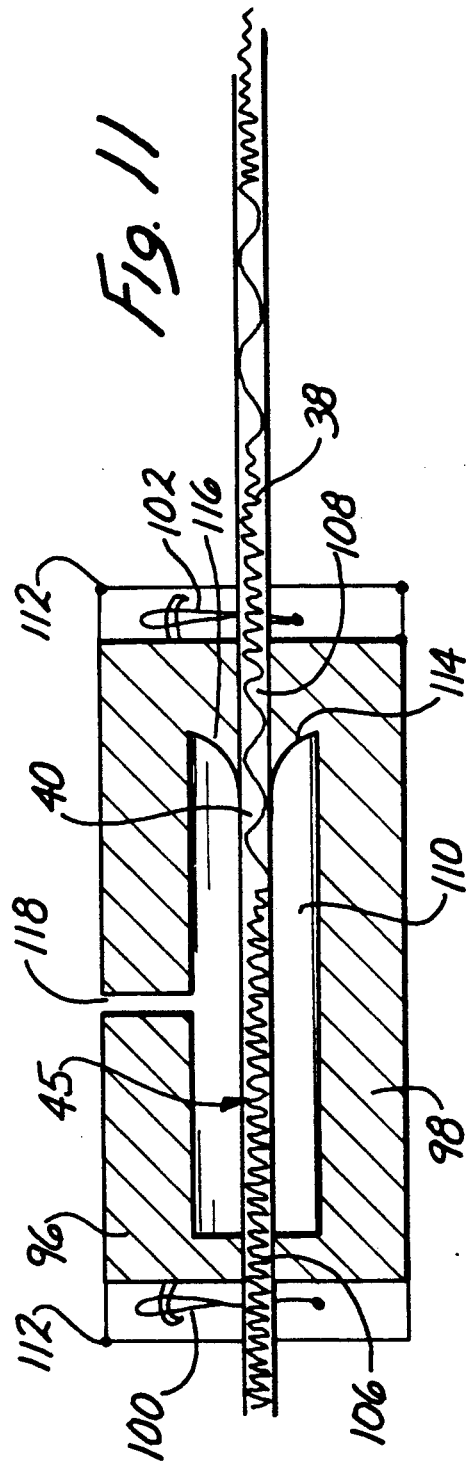
FIG. 11 is a longitudinal cross-sectional view of a ligament clamped into a mold prior to the thermomolding step in a method of the present invention.

During manufacture, the bone block(s) are thermomolded to the end(s) of the ligament to achieve the required ultimate shear load at the interface therebetween, thermomolding mold 104, as shown in FIG. 11, comprises two separable parts, cover 96 and base 98. Clamp means 100 and 102 are fixedly attached to base 98 on either side for applying tension to the portion of the heat-set ligament that lies within the mold during the thermomolding step. Application of tension to the portion of the ligament within the mold assures that substantially no crimping occurs therein during the thermomolding step.

During the thermomolding step, a preform thermoplastic bone block and one end of the heat-set ligament are placed into a heatable mold 104 so that at least a portion of end region 45 is contained therein and so that approximately one-half of bend region 40 of the ligament lies within the mold when mold cover 96 is closed. Preferably, the end region 45 extends from one end of mold 104 through slot 106 and is placed into clamp means 100 and bend region 40 and intra-articular region 38 extend through slot 108 at that other end of mold 104 and is placed into clamp 102 so that the portion of the heat-set ligament lying within mold cavity 110 is held tautly between clamp means 100 and 102. Cover 96 and base 98 cooperate when the mold is closed and fastened by a fastening means, such as fastening means 112, to position the ligament through slots 108 and 106,. which are located so that when the cooled bone block and ligament are removed from the mold, the portion(s) of the ligament not encased within the bone block protrude generally from the center of the end(s) of the formed bone block 8. In addition, mold 104 preferably has indentation means 114 and 116 located in base 98 and in cover 96, which means cooperate to form in the molded bone block a generally conically shaped depression having, at least along one side, a raised convex curve. For convenience, as shown in FIG. 11, indentation means 114 and 116 can have a reverse bend radius of from 1.5 to 3.2 mm so that the entire side of the generally conically shaped depression in the molded bone block is raised to form a convex curve.

In addition, as mentioned above, the inside surface of the cover and base of the mold is generally uneven to create an uneven surface finish on the molded bone block. Preferably the inside surface of the mold is covered with surface features (not shown) for forming pores or beads on the surface of the molded bone block of about 100 microns to about 400 microns in diameter and depth or height, as illustrated in FIGS. 8a, 8b, and 8c.

The mold is heated by any conventional means (not shown) to a temperature sufficient to melt both the preform bone block and the lower melting fibers in the ligament, but sufficiently lower than the melting point of the higher melting fiber so that the higher melting fibers in the ligament are not weakened. For C-Flex® polymer, the thermomolding temperature is usually between 160 and 190 degrees, preferably 175 degrees Centigrade. Usually the mold is maintained at the thermomolding temperature for a period of from 5 to 20 minutes, preferably about 10 minutes.

Contrary to expectation, it has been found that, when this procedure is followed, heat applied to the ligament during the thermomolding step does not damage or interfere with the results achieved during the heat-setting step. That is, the intra-articular region of the ligament retains its properties of increased elongation under load and the bend and end regions retain their respective properties of increased bend load durability and stiffness imparted during heat-setting.

After the bone block perform and ligament have been heated and molded together in the closed mold, they are allowed to cool to a temperature at which the bone block polymer and lower melting fiber solidify. Then, fastener means 112 and clamps 100 and 102 are unfastened, mold cover 96 is removed from mold base 98, and the molded bone block and ligament are removed from the mold.

During the molding step the portion of the lower melting fibers contained within the mold and immediately adjacent thereto and the low melting preform bone block become sufficiently molten that, when the molded bone block and ligament are cooled and removed from the mold, the interface between the bone block 8 and ligament 35 is rigid and provides an ultimate shear load in excess of about 1000 Newtons preferably at least 1800 Newtons. Although not required to achieve the desired ultimate shear load, the polymers in the bone block and ligament can flow together and become substantially coextensive during thermomolding. Because of the weave characteristics of the bend region of the ligament, at the point of protrusion from the molded bone block the ligament retains sufficient flexibility to conform to the permanent bend radius molded into the end of the bone block.

To form a ligament having bone blocks attached to both ends, the procedures of the thermomolding step can be repeated using a second preform bone block and the other end of the ligament. Alternatively, of course, two molds of the type above described can be used so that bone blocks are molded simultaneously onto both ends of the ligament, or two molds of the type above described can be incorporated into a single molding device for performance of the molding step.

As will be apparent to one skilled in the art, the heat-setting and thermo-setting steps can be conducted simultaneously if a composite molding device is constructed to incorporate the features of the heat-setting apparatus and the double mold hereinabove described. In such an embodiment of the invention, a preform bone block, one end region and approximately one-half of the bend region of the ligament would be clamped into each of two molds situated at either end of the ligament, and the remaining portion of the ligament would be enclosed within a heat-setting apparatus lying therebetween. In such an apparatus the heat-setting and thermomolding steps could be conducted either in sequence or simultaneously by observing the above-described temperature constraints applicable to each region of the ligament device.

Figure 12:
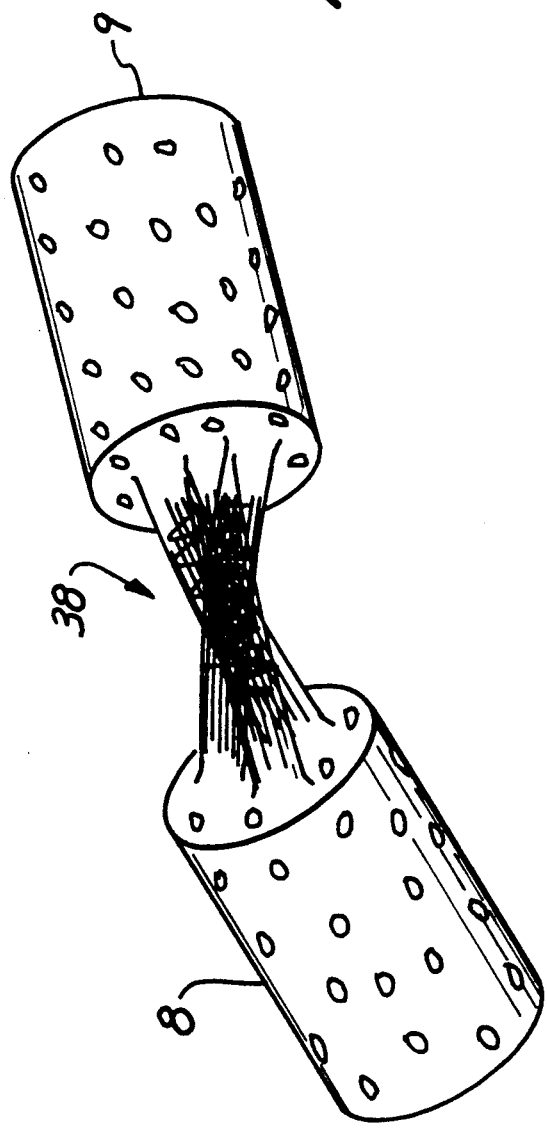
FIG. 12 is a perspective view of an artificial multibundled ligament device having two bone blocks and three ligaments in the bundle.

In yet another embodiment of the invention, illustrated in FIG. 12, a two, or, more preferably, three-bundled ligament, is employed to imitate the tripartite construction of the natural anterior cruciate ligament. However, the cross-sectional diameters of the individual ligaments making up the two or three-bundled ligament must be scaled down sufficiently that the outside dimensions of the molded bone block encasing the multi-bundled ligament is no larger than the maximum diameter of the borehole that can safely be drilled in the host bone(s), usually about 14 mm. in diameter.

To scale down the size of the ligament in this embodiment of the invention, the ligament is woven from warp and filling yarns having diameters in the range of from about 1000 to about 1500 denier, preferably 1250 to 1350, with from 100 to 230 fibers per yarn. The preferred polymer for this use is Dacron® 52B. One skilled in the art will appreciate that the weave of the ligament can also be tightened to reduce the cross-sectional area of each ligament in the bundle of ligaments molded into the bone block during the molding step.

It is known that wear particles of synthetic ligament fibers formed during use of the ligament in the body can cause irritation. For instance. Dacron ® wear particles formed during use of a synthetic anterior cruciate ligament can cause synovitis. This problem is overcome in yet another embodiment of the invention, as shown in FIG. 3, wherein the portions of the ligament not molded within the bone blocks 8 and 9 or, more preferably, the entire ligament 35 is encased within a thin sleeve of the lower melting thermoplastic polymer. Sleeve 116 is a solid tube of the lower melting polymer having a wall thickness of from 0.05 to about 1.0 mm, and preferably of from 0.25 to 1.0 mm. The inside diameter of the tube is slightly larger than the outside diameter of the woven fiber ligament. Therefore the inside diameter of the tube generally ranges from about 4 to 8 mm.

The sleeve is slipped onto the ligament and thermomolded thereto by any conventional type of thermomolding device (not shown) while care is taken that the temperature of the mold be raised high enough to melt the lower melting polymer in the sleeve and in the ligament sufficiently to cause secure attachment therebetween, but not so high as to melt or otherwise destroy integrity of the higher melting fiber. Preferably, the sleeve 116 is thermomolded onto the ligament prior to the molding step described above wherein the ligament and the preform bone block are placed into mold 104 and thermomolded together. Optionally, however, the sleeve can be slipped onto the ligament before the ligament and preform bone block are placed into the mold for the molding step and the sleeve can be molded onto the ligament at the same time that the bone block(s) are attached thereto.

In an alternative and less preferred embodiment of the invention, a substrate ligament is woven as described herein except that a single type of inelastic, heat-settable biocompatible fiber, such as Dacron ® 52, is used, rather than the commingled higher and lower melting fibers. This less preferred embodiment of the invention differs further in forming the bone blocks from a flexible, biocompatible thermoset resin. As used herein, a thermoset resin is a polymer formulation that. upon being heated to the thermoset temperature, becomes a rigid solid that cannot be reheated and reformed. Examples of suitable thermoset resins for use in this embodiment of the invention are the acrylics and polyurethanes, for example polymethyl-methacrylate, and the aliphatic resin systems, such as various formulations of Eponex ® 1510, manufactured by Shell Chemical Company, Houston, TX.

During manufacture, the single fiber ligament is heat-set to improve elasticity in the intra-articular region, either before or during the molding step, as above described, and optionally, but preferably, the portion of the ligament not contained within the bone blocks is sheathed by thermomolding thereto a sleeve of a lower melting, thermoplastic polymer, as described above. However, it should be noted that in this embodiment the polymers in the ligament and bone block are not attached together by thermomolding to provide the requisite strength at the interface therebetween. Rather, attachment of the ligament to the bone block(s) is made when a liquid resin is poured into the mold cavity around the portion of the ligament contained therein and allowed to set at the thermoset temperature. It is essential, therefore, that the liquid resin flow into the interstices in the weave of the ligament so that during the setting step a strong attachment of the bone block to the ligament is formed at the interface. Therefore, the sleeve of lower melting polymer should not extend over the entire portion of the ligament that interfaces with the bone block. Preferably, the sleeve extends within the bone block a distance of only about 3 to 7 cm.

The mold required to make the ligament devices of this embodiment has a liquid port 118 and is made to hold liquid when closed and fastened. Before the setting step, the ligament is stretched between clamps 100 and 102 of mold 104, and mold cover 96 is closed over mold base 98 and fasteners 112 are fastened. The mold is then filled by pouring liquid resin into liquid port 118. To solidify the bone block and fixedly attach it to the ligament, the mold is maintained at the thermosetting temperature by any conventional method of heating, if required, and held at temperature for a time sufficient to complete the thermosetting reaction within the resin. The thermosetting temperature varies according to the specific resin used and can be determined empirically. Usually, however, the thermosetting reaction temperature is between about 24 and 100 degrees Centigrade.

The invention is further illustrated by the following example of the method of making a replacement ligament device having thermoset bone blocks attached thereto:

A single fiber ligament preform was woven from Dacron ® 52B fiber using a standard narrow fiber loom with a two-inch beam containing 234 ends of 350 denier yarn. The yarn, which consisted of 100 filaments each approximately 19 microns in diameter, was twisted to 6 turns/inch in the Z direction. The fiber was drawn into the loom using the weave pattern shown in FIG. 13, and was woven with a warp tension of approximately 50 lbs., a filling tension of approximately 0.5 lbs. and a pick setting of 25 picks per inch to produce a section of ligament having the characteristics of an end region 7 cm in length having a rectangular cross-section of 4 mm in width and 2.5 mm in thickness. At a particular point in the weaving, the warp tension was reduced to 10 pounds, resulting in an increase in the width of the woven product to 6 mm, and a decrease in the thickness of the product to 1.5 mm. There was also an increase in the number of picks per inch, since the takeup of the woven fiber was less positive under the low tension conditions. After a certain number of picks had been inserted, the warp tension was again increased to 50 lbs., and the weave structure stabilized again at the original dimensions. This sequence of high and low tension was repeated to produce a chain of samples. each containing high crimp warp yarn with high elongation characteristics, bounded by two regions each containing low crimp warp yarns, with low elongation characteristics.

Thermoset bone blocks were attached to the ligament preform and the strength of the attachment thereto was tested as follows: The all Dacron ® ligament preform was placed into a prototype two part mold cavity of the type illustrated in FIG. 11. A two-part orthodontic acrylic resin system (manufactured by L. D. Caulk Company Milford, DE) was mixed to contain approximately 30% by volume of resin powder and 70% by volume of liquid catalyst so as to form a slurry having a viscosity of about 70 centipoise. The low viscosity slurry was poured into the mold and allowed to cure at an ambient temperature of 24 degrees Centigrade for approximately two hours. The ligament-bone block device was then removed from the mold. Shear strength testing of the interface was performed the following day using a calibrated Instron Materials Tester (manufactured in Boston, MA) and a fixture for holding the bone block with the ligament suspended therefrom while a load is applied to the suspended ligament. The load was increased at increments of 200 mm per minute. The shear load upon the device at failure of the interface was 3490 Newtons.

While the invention has been described in connection with certain preferred embodiments, it is not intended to be so limited, but is intended to encompass modifications and variations thereof within the spirit and scope of the appended claims.

We claim:

1. An artificial ligament device having a generally multilayered or tubular woven ligament and being adapted for joining the ends of two bones, at least one of the bones having a tunnel extending therethrough, said device comprising:
   (a) a ligament having
      (1) an intra-articular region adapted for disposition between the respective ends of the two bones;
      (2) at least one bend region juxtaposed to the intra-articular region and adapted for encasement within a bone block and being located generally where the ligament exits and runs within the bone block; and
      (3) at least one end region juxtaposed to the bend region and adapted for fixed encasement within the bone block;
      a plurality of warp yarns extending at least through the bend region; and
      a fill yarn woven through the warp yarns in a density dependent upon the number of picks per inch in the weave; and
      a pick density in the bend region being not greater than one-third the pick density in the intra-articular region; and
   (b) at least one bone block adapted for insertion into the bone tunnel and having fixedly encased therein the end region and a portion of the bend region, said bone block providing a permanent bend radius for the bend region at the point of exit from the bone block.

2. The artificial ligament recited in claim 1 wherein the pick density in the bend region is less than one-fifth the pick density in the end region and wherein the exposed portion of the ligament is encased within a thin polymer sleeve.

3. The artificial ligament recited in claim 1 wherein the number of picks per inch in the bend region is not more than eight and wherein the bone block comprises a thermoset resin and the resin runs within the interstices in the woven ligament.

4. The artificial ligament recited in claim 1 wherein the number of picks per inch in the bend region is not more than three and wherein the bone block is thermomolded to the ligament.

5. The artificial ligament recited in claim 1 wherein the number of picks per inch in the bend region is not more than one.

6. The artificial ligament recited in claim 1 further comprising:
   marker means disposed relative to the bend region for providing a visual indication of the location of the bend region.

7. The artificial ligament recited in claim 6 wherein the marker means includes a thread disposed transverse to the warp yarns at each end of the bend region.

8. An artificial ligament device adapted for joining the ends of two bones, at least one of the bones having a tunnel extending therethrough, said device comprising:
   (a) a ligament of a generally multilayered or tubular woven structure having warp and filler yarns wherein the warp yarns are composite, having a higher melting polymer core within a substantially continuous covering of a thermoplastic lower melting polymer, said ligament comprising:
      (1) an intra-articular region adapted for disposition between the respective ends of the two bones;
      (2) at least one bend region Juxtaposed to the intra-articular region and being located generally where the ligament exits and runs within the bone block;
      (3) at least one end region juxtaposed to the bend region and adapted for thermomold encasement within a bone block;
      a plurality of warp yarns extending continuously through the intra-articular region, and the bend region;
      a fill yarn woven through the warp yarns with a pick density in the bend region of not more than eight picks per inch; and
      each of the warp and fill yarns consisting of filaments numbering in a range between about 20 and 200 filaments and having a density in the range of about 50 to 1100 denier; and
   (b) at least one bone block adapted for insertion into the bone tunnel and being thermomolded to the ligament so as to provide a permanent bend radius for the bend region at the point of exit of the bend region from the bone block.

9. The artificial ligament recited in claim 8 wherein each of the warp and fill yarns consists of filaments numbering in a range of about 50 to 150 filaments and a diameter in a range of about 50 to 150 denier and wherein the bone block comprises the lower melting polymer.

10. The artificial ligament recited in claim 9 wherein each of the warp and fill yarns consists of about 100 filaments and has a diameter of about 350 denier.

11. The artificial ligament device of claim 8 further comprising a thin polymer sleeve encasing the portion of the ligament extending from the bone block.

12. The artificial ligament device of claim 11 wherein the number of bone blocks, bend regions and end regions is two and said bone block, bend regions and end regions are symmetrically arranged about a central intra-articular region and wherein the sleeve is thermomolded to encase the portion of the ligament exposed between the bone blocks.

13. A replacement ligament device, which device comprises:
   (a) an artificial ligament of a generally multilayered or tubular woven structure having warp and filling yarns wherein the warp yarns are composite, having a higher melting polymer core with a substantially continuous covering of a thermoplastic lower melting polymer, said ligament comprising
      (1) an intra-articular region adapted for disposition between the respective ends of the two bones and having woven, highly crimped warp yarns wherein the degree of crimping of the warp yarns is such that, within the range of normal physiological loads, the intra-articular region has an elongation at failure and an elasticity substantially the same as those of a normal natural ligament of the type that the artificial ligament is intended to replace;

(2) at least one bend region juxtaposed to the intra-articular region wherein the degree of crimping of the warp yarns is substantially less than in the intra-articular region and wherein the pick density is from zero to eight picks per inch; and (3) at least one end region juxtaposed to the bend region at the end of the ligament wherein the end region is woven under a relatively high warp tension and wherein the degree of crimping is substantially less than in the intra-articular region for providing a strong, stiff matrix for thermomold attachment of the end region to a bone block; and (b) at least one bone block of a thermoplastic, low melting polymer wherein the bone block is sized for emplacement into a bone tunnel drilled into a bone to which a normal natural ligament of the type that the artificial ligament is intended to replace would attach, and wherein the bone block is thermomolded to said ligament so that about one half of the bend region and the contiguous portion of the end region of the ligament are fixedly encased within the bone block and wherein the bone block provides a permanent bend radius for the ligament at the point of attachment to the ligament, said bend radius being sized for enhancing the bending fatigue life of the ligament.

14. The device of claim 13 comprising two bone blocks, one thermomolded to each end of the ligament so as to encase therein respectively about one-half of a bend region and the contiguous portion of the end region of the ligament and wherein the thermomold interface between the bone block and the ligament has an ultimate shear load in excess of about 1800 Newtons.

15. The device of claim 13 wherein the lower melting fiber and the bone block consist essentially of the same biocompatible, thermoplastic polymer.

16. The device of claim 13 wherein the bone block and the lower melting fiber comprise a silicone-modified thermoplastic elastomer.

17. The device of claim 13 wherein the intra-articular region has a percent elongation at failure of from about 10% to about 50% and an elasticity which enables it to recover to substantially its original dimensions after being subjected to repeated cycles of 25% of the tensile failure load and wherein the mechanical stiffness of the bone block is at least about 1500 Newtons per millimeter and the ultimate shear load of the thermomold interface between the ligament and the bond block is at least about 1000 Newtons.

18. The device of claim 13 wherein the warp and filling yarns are prepared from polymer fibers which exhibit low elongations under load and wherein the bone block is elongate and has the shape in the cross-section selected from the group consisting of a circle, square or rectangle.

19. The device of claim 16, wherein the warp and filling yarns have diameters from about 50 to about 1100 denier, and contain from about 20 to about 200 filaments per yarn.

20. The device of claim 14 wherein the bone block has the shape of a solid right cylinder having a right cross-sectional diameter of from about 6 to 14 mm and the ultimate shear load of the interface is at least about 1800 Newtons.

21. The device of claim 20 wherein the diameter is from about 8 to 12 mm..

22. The device of claim 17 wherein the bone block has the shape of a solid right cylinder with a conical depression in the end at the point from which the ligament exits, wherein the side of the cone is convex to provide the permanent bend radius.

23. The device of claim 22 wherein the bend radius is from about 1.5 to 1.3 mm.

24. The device of claim 16 wherein the filling yarns are prepared solely from the higher melting polymer.

25. The device of claim 13 wherein the warp density of the intra-articular region ranges from about 800 to about 1200 yarns per inch and the pick density of the intra-articular region ranges from about 40 to about 70 picks per inch and the pick density of the bend region is not more than one.

26. The device of claim 13 wherein the weave pattern of the intra-articular region is a 5-1-1-5 broken twill.

27. The device of claim 25 wherein the warp density of the intra-articular region is about 1000 yarns per inch and the pick density of the intra-articular region ranges from about 50 to about 60 picks per inch.

28. The device of claim 13 wherein the warp tension employed during the weaving of the intra-articular region is from about 0.01 to about 0.05 lb. per yarn end, and the filling yarn tension is from about 0.05 to about 0.5 lb. per yarn end.

29. The device of claim 15 wherein the ligament is subjected to a post-weaving heat-setting step prior to being thermomolded into the bone block, wherein the heat-setting step is to increase the elongation under load of the intra-articular region and to increase the stiffness of the end region.

30. The device of claim 13 wherein the ligament is subjected to a post-weaving heat-setting step to increase the elongation under load of the intra-articular region and to increase the stiffness of the end region contiguous thereto.

31. The device of claim 29 or 30 wherein the intra-articular region is substantially unconstrained during the heat-setting step, thereby allowing the warp yarns to crimp and the weft yarns to remain uncrimped, producing a high elongation under load, and the bend and end regions are constrained against longitudinal movement, thereby inhibiting the warp yarns from crimping and producing a low elongation under load.

32. The device of claim 29 or 30 wherein the elongation under load of the bend region is less than about 15% at failure and the elongation under load of the intra-articular region is from about 10 to 50% at failure.

33. The device of claim 29 or 30 wherein the composite yarn is formed during the post-weaving heat-setting step from a substrate yarn comprising commingled lower melting point fibers and higher melting point fibers, the temperature at the heat-setting step being sufficiently above the melting temperature of the lower melting polymer, but sufficiently below the melting temperature of the higher melting polymer, to cause the lower melting fibers to melt to form a coating substantially surrounding the higher melting fibers without weakening the higher melting fibers.

34. The device of claim 15 wherein the higher melting fiber is polyethylene terephthalate and the lower melting fiber is styrene-ethylene/butylene, styrene block copolymer with polydimethylsiloxane modifiers.

35. The device of claim 13 wherein the intra-articular region has a relatively small cross-sectional area, a high aspect ratio approximating that of the natural ligament being replaced and a length of from about 30 to about 36 mm.

36. The device of claim 35 wherein the cross-sectional area is circular with a diameter of from about 4 to 8 mm and wherein the tensile strength of the intra-articular region is from 2000 to about 2250 Newtons.

37. The device of claim 36 wherein the cross-sectional area is circular with a diameter of from about 4 to 5 mm and the tensile strength is about 3500 Newtons.

38. The device of claim 33 wherein the warp tension during the weaving of the intra-articular region is from about 0.01 to about 0.05 lb. per yarn end, and the filling tension is from about 0.05 to about 0.5 lb. per yarn end.

39. The device of claim 15 wherein the higher melting fiber comprises a polyester having a melting point from 10 to 100 Centigrade degrees higher than the melting point of the lower melting fiber.

40. The device of claim 13 wherein the surface of the bone block is uneven to promote bony ingrowth therein.

41. The device of claim 40 wherein the uneven surface of the bone block comprises fibrous protuberances.

42. The device of claim 40 wherein the uneven surface of the bone block is porous.

43. The device of claim 42 wherein the pores in the porous surface are from about 100 to about 400 microns in diameter and in depth.

44. The device of claim 40 wherein the uneven surface of the bone block is beaded.

45. The device of claim 44 wherein the beaded surface comprises raised beads of about 200 to about 400 microns in diameter and in height.

46. The device of claim 13 wherein the ligament further comprises a thin sleeve of the lower melting polymer thermomolded thereon so as to completely encase the portion of the ligament extending from the bone block.

47. The device of claim 46 wherein the sleeve of lower melting polymer has a wall thickness of from about 0.05 to about 1.0 mm.

48. The device of claim 47 wherein the sleeve of lower melting polymer has a wall thickness of from about 0.25 to about 1.0 mm.

49. The device of claim 13 wherein the surface of the bone block further comprises a thin coating of osteoconductive material.

50. A replacement ligament device being adapted for joining the ends of two bones, which device comprises:
  (a) a multibundled artificial ligament having a plurality of ligaments in the bundle wherein each ligament is of a generally multilayered or tubular woven structure having warp and filler yarns, said ligament comprising
    (1) an intra-articular region adapted for disposition between the respective ends of the two bones;
    (2) bend regions juxtaposed to the intra-articular region wherein the elongation under load is substantially less and the flexibility is substantially greater than that of the intra-articular region;
    (3) end regions juxtaposed to the bend regions at the two ends of the ligament for providing a strong, stiff matrix for fixed encasement within a bone block; and
  (b) two bone blocks sized for emplacement into a bone tunnel drilled into one of the bones, wherein each bone block encases and is fixedly attached to one end region and a portion of the contiguous bend region and provides a permanent bend radius for the bend region at the point of attachment to the ligament, said bend radius being sized for enhancing the bending fatigue life of the ligament.
  wherein the device is adapted so that the bend regions are situated at the point at which the bone block exits from a tunnel in the respective bones.

51. The device of claim 49 wherein the number of ligaments is two.

52. The device of claim 49 wherein the number of ligaments is three.

53. The device of claim 50 wherein the warp yarn has a denier of from about 1000 to about 1500.

54. A replacement ligament device being adapted for joining the ends of two bones, which device comprises:
  (a) a multibundled artificial ligament having a plurality of ligaments in the bundle wherein each ligament is of a generally multilayered or tubular woven structure having warp and filler yarns wherein the warp yarns are composite, having a higher melting polymer core with a substantially continuous covering of a thermoplastic lower melting polymer, said ligament comprising:
    (1) an intra-articular region adapted for disposition between the respective ends of the two bones and having highly crimped warp yarns wherein the degree of crimping of the warp yarns is such that, within the range of normal physiological loads, the intra-articular region has an elongation at failure and an elasticity substantially the same as those of a normal natural ligament of the type that the artificial ligament is intended to replace;
    (2) bend regions juxtaposed to the intra-articular region wherein the degree of crimping of the warp yarns is substantially less than in the intra-articular region and the pick density is from zero to 8 picks per inch, such that the elongation under load is substantially less and the flexibility is substantially greater than that of the intra-articular region;
    (3) end regions juxtaposed to the bend regions at the two ends of the ligament wherein the end region is woven under a relatively high warp tension and wherein the degree of crimping is substantially less than in the intra-articular region for providing a strong, stiff matrix for thermomold attachment of the end regions to a bone block; and
  (b) two bone blocks of a thermoplastic, low melting polymer wherein the bone block is sized for emplacement into a bone tunnel drilled into one of the bones, and wherein each bone block has thermomolded thereinto one end of each ligament so that about one half of one bend region and the contiguous portion of one end region of the ligament are fixedly encased within the bone block and wherein the bone block provides a permanent bend radius at the point of attachment to bend region, said bend radius being sized for enhancing the bending fatigue life of the ligament.
  wherein the device is adapted so that the bend regions are situated at the point at which the bone block exits from the tunnel in the respective bone.

55. The device of claim 54 wherein the lower melting fiber and the bone block consist essentially of the same biocompatible, thermoplastic polymer, wherein the number of ligaments is three, and wherein the diameter of the warp and filler yarns ranges from about 1000 to 1500 and the number of filaments ranges from about 100 to 230.

56. The device of claim 55 wherein the bone block and the lower melting fiber comprise a silicone-modified thermoplastic elastomer.

57. The device of claim 54 wherein the intra-articular region has a percent elongation at failure of from about 10% to about 50% and an elasticity which enables it to recover to substantially its original dimensions after being subjected to repeated cycles of 25% the tensile failure load and wherein the mechanical stiffness of the bone block is at least about 1500 Newtons per millimeter and the ultimate shear load of the thermomold interface between the ligament and the bond block is at least about 1000 Newtons.

58. The device of claim 54 wherein the warp and filling yarns are prepared from polymer fibers which exhibit low elongations under load and wherein the bone block is elongate and has the shape in the cross-section selected from the group consisting of a circle, square or rectangle.

59. The device of claim 56, wherein the warp and filling yarns have diameters from about 1250 to about 1350 denier, and contain from about 100 to about 230 filaments per yarn.

60. The device of claim 56 wherein the bone block has the shape of a solid right cylinder having a right cross-sectional diameter of from about 6 to 14 mm.

61. The device of claim 60 wherein the diameter of the bone block is from about 8 to 12 mm.

62. The device of claim 57 wherein the bone block has the shape of a solid right cylinder with a conical depression in the end at the point from which the ligament exits, wherein the side of the cone is convex to provide the permanent bend radius.

63. The device of claim 62 wherein the bend radius is from about 1.5 to 1.3 mm.

64. The device of claim 56 wherein the filling yarns are prepared solely from the higher melting polymer.

65. The device of claim 54 wherein the warp density of the intra-articular region ranges from about 800 to about 1200 yarns per inch and the pick density of the intra-articular region ranges from about 40 to about 70 picks per inch and the pick density of the bend region is not more than one.

66. The device of claim 54 wherein the weave pattern of the intra-articular region is a 5-1-1-5 broken twill.

67. The device of claim 54 wherein the warp density of the intra-articular region is about 1000 yarns per inch and the pick density of the intra-articular region ranges from about 50 to about 60 picks per inch.

68. The device of claim 54 wherein the warp tension employed during the weaving of the intra-articular region is from about 0.01 to about 0.05 lb. per yarn end, and the filling yarn tension is from about 0.05 to about 0.5 lb. per yarn end.

69. The device of claim 54 wherein the ligament is subjected to a post-weaving heat-setting step prior to being thermomolded into the bone block, wherein the heat-setting step is to increase the elongation under load of the intra-articular region and to increase the stiffness of the end region.

70. The device of claim 54 wherein the ligament is subjected to a post-weaving heat-setting step to increase the elongation under load of the intra-articular region and to increase the stiffness of the end region contiguous thereto.

71. The device of claim 69 or 70 wherein the intra-articular region is substantially unconstrained during the heat-setting step, thereby allowing the warp yarns to crimp and the weft yarns to remain uncrimped, producing a high elongation under load, and the bend and end regions are constrained against longitudinal movement, thereby inhibiting the warp yarns from crimping and producing a low elongation under load.

72. The device of claim 69 or 70 wherein the elongation under load of the bend region is less than about 15% at failure and the elongation under load of the intra-articular region is from about 10 to 50% at failure.

73. The device of claim 69 or 70 wherein the composite yarn is formed during the post-weaving heat-setting step from a substrate yarn comprising commingled lower melting point fibers and higher melting point fibers, the temperature at the heat-setting step being sufficiently above the melting temperature of the lower melting polymer, but sufficiently below the melting temperature of the higher melting polymer, to cause the lower melting fibers to melt to form a coating substantially surrounding the higher melting fibers without weakening the higher melting fibers.

74. The device of claim 54 wherein the higher melting fiber is polyethylene terephthalate and the lower melting fiber is styrene-ethylene/butylene, styrene block copolymer with polydimethylsiloxane modifiers.

75. The device of claim 54 wherein the higher melting fiber comprises a polyester having a melting point at least 10 Centigrade degrees higher than the melting point of the lower melting fiber.

76. The device of claim 54 wherein the surface of the bone block is uneven to promote bony ingrowth therein.

77. The device of claim 54 wherein the ligament further comprises a thin sleeve of the lower melting polymer thermomolded thereon so as to completely encase the portion of the ligament extending from the bone block.

78. The device of claim 71 wherein the sleeve of lower melting polymer has a wall thickness of from about 0.05 to about 1.0 mm.

79. The device of claim 11 wherein the surface of the bone blocks further comprises a thin coating of osteoconductive material.

80. An improved method for making an artificial ligament device adapted to replace a natural ligament extending between the ends of two bones, including the steps of:
   providing a plurality of warp yarns extending longitudinally of the ligament in both an end region and a bend region of the ligament;
   weaving a fill yarn into the warp yarns in a density dependent upon the number of picks per inch;
   controlling the weave to provide a particular number of picks per inch in the intra-articular region;
   reducing the number of picks per inch to not more than one-third the particular number during the weaving of the bend region; and
   molding a polymer bone block around the end region and a portion of the bend region so as to fixedly encase said regions and provide a fixed bend radius for the bend region at the point of exit from the bone block.

81. The method of claim 80 further comprising the steps of (1) heatsetting the ligament to provide a substantial crimp in the warp yarn in the intra-articular region while leaving the warp yarn in the remainder of the ligament substantially uncrimped and (2) thermomolding a thin polymer sleeve around the portion of the ligament extending from the bone block.

82. The method of claim 81 wherein the warp yarns used in the weaving steps are formed from commingled higher melting and thermoplastic, lower melting fibers and the bone block is formed from a thermoplastic, lower melting polymer wherein during the molding step the lower melting polymers are heated sufficiently to cause the warp yarns to reform into a composite, having a higher melting polymer core with a substantially continuous covering of a thermoplastic lower melting polymer and to cause the bone block to be thermomolded to the ligament.

83. The method of claim 81 wherein the bone block is formed from a thermoset resin and wherein during the molding step the resin flows into the interstices in the weave of the end and bend regions of the ligament and is thermoset therein.

* * * * *